United States Patent [19]

Ruegg et al.

[11] 4,129,280
[45] Dec. 12, 1978

[54] PIVOT MECHANISM

[75] Inventors: André Ruegg, Zürich; Wilfried Beck, Winterthur, both of Switzerland

[73] Assignee: Contraves AG, Zürich, Switzerland

[21] Appl. No.: 864,484

[22] Filed: Dec. 27, 1977

[30] Foreign Application Priority Data

Feb. 7, 1977 [CH] Switzerland ............... 1447/77

[51] Int. Cl.² ........................................... F16M 13/12
[52] U.S. Cl. ................................. 248/183; 248/278; 403/57
[58] Field of Search ............... 248/122, 179, 183, 184, 248/278, 515; 403/55, 57

[56] References Cited

U.S. PATENT DOCUMENTS

| | | | |
|---|---|---|---|
| 977,658 | 12/1910 | Leaver | 248/122 X |
| 1,285,291 | 11/1918 | McLaughlin | 403/57 X |
| 1,514,205 | 11/1924 | Fitzgerald | 248/278 X |
| 2,362,100 | 11/1944 | Schwartz | 248/278 X |

Primary Examiner—William H. Schultz
Attorney, Agent, or Firm—Werner W. Kleeman

[57] ABSTRACT

A pivot mechanism for a housing laterally arranged at a support, such as a stand or the like, especially a housing for a medical instrument, comprising a first axle body and a second axle body, the second axle body being rotatably mounted at one side or end in the first axle body and at the other side or end is capable of being operatively connected with the housing. The first axle body and the second axle body are mounted in a headpiece such that the housing is horizontally rotatable about an essentially vertical lengthwise axis of the first axle body and vertically pivotable about an essentially horizontal lengthwise axis of the second axle body. The headpiece has at least one friction surface for the horizontal rotational movement and further friction surfaces for the vertical pivotal movement. For braking such movements there is provided but a single resilient element such as a compression or pressure spring.

9 Claims, 5 Drawing Figures

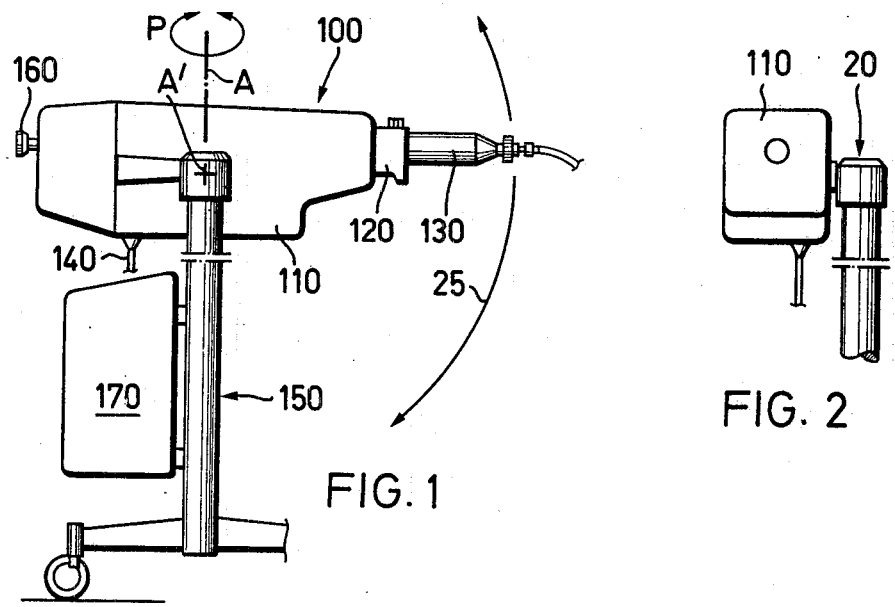
FIG. 1
FIG. 2
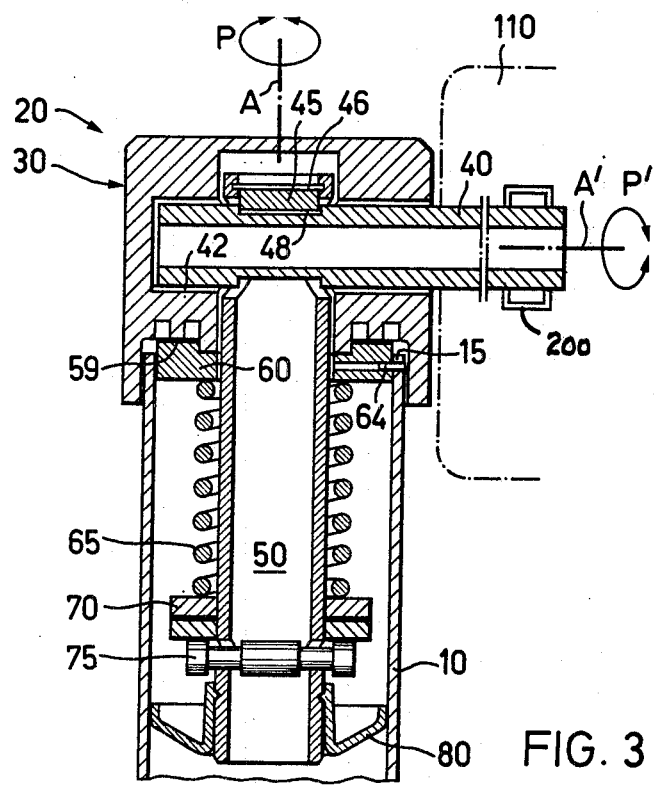
FIG. 3

PIVOT MECHANISM

BACKGROUND OF THE INVENTION

The present invention relates to a new and improved construction of a pivot mechanism for a housing which is laterally arranged at a stand or upright member, especially a pivot mechanism for the housing of a medical instrument.

SUMMARY OF THE INVENTION

It is a primary object of the present invention to provide a device for the most extensive unlimited adjustment of a housing arranged laterally of a stand or the like, and which can be connected with the stand without the need for additional attachment means and wherein the housing can be positioned in horizontal and vertical direction while retaining the requisite stability and without the need to adjust special screws or fixing means for retaining the housing in the adjusted position, and further, enabling rocking or rotating the housing into another desired position without the need to loosen any such means.

Still a further significant object of the present invention aims at a new and improved construction of a pivot mechanism for securing a housing to a stand in a positive manner, while enabling selective adjustments of the housing into different desired positions in a most simple and easy fashion without the need to undertake complicated fixation manipulations, while ensuring for stability of the housing in the adjusted position.

Yet a further significant object of the present invention aims at providing a novel arrangement for pivotably mounting a housing at a stand or upright member, allowing for increased mobility of the housing, when desired into various selected positions, without having to manipulate special fixing elements or having to release such whenever it is desired to again move the housing into a different position.

Now in order to implement these and still further objects of the invention, which will become more readily apparent as the description proceeds, the pivot mechanism or arrangement of the present development is generally of the type comprising a first axle body and a second axle body, the second axle body being rotatably mounted at one side in the first axle body and is operatively connected at its other side with the housing. According to important features of the invention, the first axle body and the second axle body are mounted in a headpiece or element in such a manner that the housing can be horizontally rotated about an essentially vertical lengthwise axis of the first axle body and vertically pivoted about an essentially horizontal lengthwise axis of the second axle body. The headpiece is provided with at least one friction surface for the horizontal rotational movement and further friction surfaces for the vertical pivotal movement. In order to brake the aforementioned movements there need only be provided a single pressure or compression spring.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 1 is a schematic illustration of a medical instrument, here shown as an injection device secured to a stand or upright member by means of a pivot mechanism constructed according to the teachings of the present invention;

FIG. 2 is a fragmentary side view of part of the stand together with the injector housing of the arrangement of FIG. 1;

FIG. 3 is an enlarged fragmentary sectional view of the pivot mechanism for connecting the injector housing with the stand;

DETAILED DESCRIPTION OF THE PREFERRED EMBODIMENTS

Figure 4:
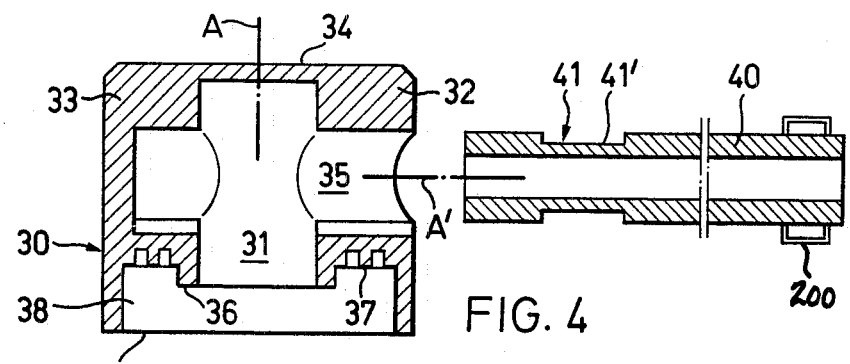
FIG. 4 is an exploded sectional view showing details of the pivot mechanism of FIG. 3 in its disassembled state.

Describing now the drawings, in FIG. 1 there is shown schematically a medical instrument or device, especially an injector device or injector 100, which will be seen to have an injector housing 110 secured to a stand or upright member 150 which can be mounted in conventional fashion upon casters or rolls as shown. Mounting of the injector housing 110 at the stand or upright member 150 is accomplished by means of a pivot mechanism 20 constituting the crux of the invention, details of which will be considered more fully hereinafter in conjunction with FIGS. 3, 4 and 4a. At this point it is remarked that the injector housing 110 is provided at one side with a holder 120 for an injection syringe 130 and at the other oppositely situated side with an adjustment knob 160 or other equivalent or suitable structure for a not particularly shown but conventional volume limiting device. At the preferably mobile stand 150 there is additionally secured a control and operating console or panel 170 which is connected by the partially shown control cable 140 with the housing 110. As mentioned, the important part of the invention is the pivot mechanism 20 and therefore details of the medical instrument or device 100 and its control are unimportant for appreciating the underlying concepts of the present development, particularly since the pivot mechanism is not limited for use with the housing of a medical instrument, but can be employed to advantage with other structures where it is desired to pivot and move a structure and fix the same in position in a manner as will be described more fully hereinafter.

Now in FIG. 2 there is shown part of the injection device or injector 100 in side view without the control and operating console 170. The housing 110 will be seen to be arranged laterally of the here only partially shown stand 150, housing 110 being operatively connected with such stand 150 by means of the pivot mechanism or pivot arrangement 20 serving as the connection element between stand 150 and housing 110.

Now as indicated in FIG. 1 by means of the pivot mechanism 20 the housing 110 can be both rotated about an essentially vertical axis A in the direction of the double-headed arrow P and also can be rocked or pivoted in the direction of the double-headed arrow 25 about an essentially horizontal axis A'. Further, the pivotal range of the housing 110, indicated by the double-headed arrow 25, is extensively unlimited.

FIG. 3 shows on an enlarged scale and in sectional view the pivot mechanism 20, which will be seen to comprise a headpiece or element 30, a first axle body or element 50, a second axle body or element 40 and a centering ring 80 arranged at the lower end of the first axle body 50. By means of the centering ring 80 the pivot mechanism 20 is centered and guided in the upstanding column or tube 10 of the stand 150.

Figure 4A:
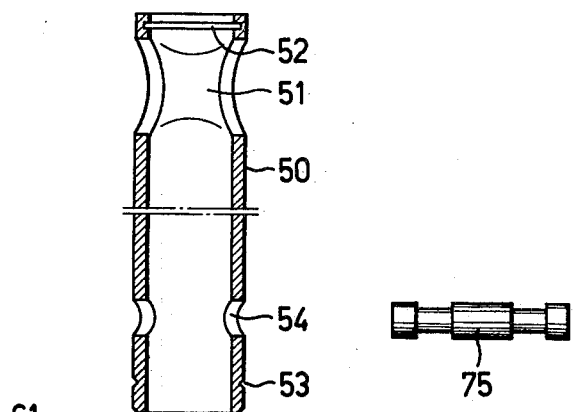
FIG. 4a is a detail of part of the pivot mechanism shown in FIGS. 3 and 4.
Figure 4A:
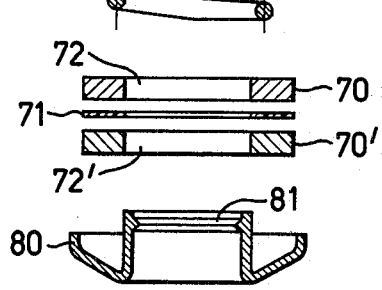
Figure 4A:
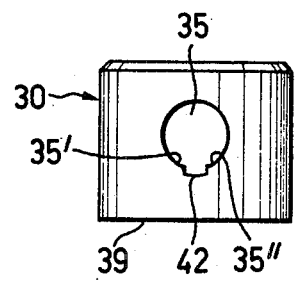

FIG. 4 illustrates in exploded sectional view all of the individual elements or components of the pivot mechanism 20 of the present development, and which will be considered fully in the description to follow.

The headpiece 30 which is preferably of cylindrical configuration will be seen to comprise a bore 31, constructed as a blindhole bore, extending in the direction of the vertical axis A as well as a bore 35 oriented transversely with respect to the vertical axis A and extending in the direction of the horizontal axis A'. Bore 35 piercingly extends through one side of the wall 32 of the headpiece 30 and terminates at the other oppositely situated side in the wall 33 in the form of a blindhole bore. At the upper end 34 the headpiece 30 is preferably closed, as shown, whereas the lower side or end 39 is extensively open and has a recess 38. This recess 38 is internally provided with a substantially ring-shaped projection or shoulder 36 as well as a substantially ring-shaped or annular contact or friction surface 37. In the side view of FIG. 4a the headpiece 30 has been shown on a smaller scale. There will be recognized the bore 35 which at the side confronting the open side or face 39 of the headpiece 30 is equipped with a groove-like recess or depression 42 extending in radial direction.

The second axle body or element 40 which, for instance, is formed from a cylindrical tube or pipe and defines the horizontal axis A', possesses at one side and at the outer circumference thereof a peripheral recess or groove 41 providing a friction surface serving to receive a sliding element 45, whereas the other oppositely situated side or end is suitably structured to have any appropriate means 200 for receiving and attaching the housing 110 in any convenient fashion.

The sliding element 45 has a recess 47, preferably of arc-shaped configuration, which is constructed such that in the assembled condition the sliding element or slide member 45 only bears with two edges at the surface 41' of the circumferentially extending recess 41 of the second axle body 40, so that an air gap 48 is formed between the surface 41' of the recess 41 and the inner edge 47' of the recess 47, as best seen by referring to FIG. 3.

The first axle body 50 which is likewise preferably formed of a cylindrical tube or pipe and defines the vertical axis A, is provided at the upper region thereof with an inner, circumferentially extending groove 52 for the reception of a securing or safety ring 46 and with a bore 51 which piercingly extends through the axle body 50 and serving for the reception of the second axle body 40. At its lower region the axle body 50 is equipped with a bore 54 piercingly extending through such axle body and serving for the reception of a bolt 75. This lower region of the axle body 50 is also provided with an outer ring-shaped or annular groove 53 for receiving and mounting centering ring 80.

Also, by referring to FIG. 4 there will be recognized a pressure element, here shown in the form of a pressure ring 60 having a sliding surface 61 and an opening 62. There is also provided a pressure exerting element, here in the form of a conventional pressure or compression spring 65, two discs 70 and 70' each having an opening 72 and 72', respectively, and separated from one another by a sliding disc 71. The bolt 75 is insertable into the opening 54 of the axle body 50, and there will be additionally recognized that the centering ring 80 has an internal or inner ring-shaped bead 81. The pressure or compression ring 60 is furthermore provided with at least three bores 63 arranged in distributed fashion at the periphery thereof and each serving for the reception of a cylindrical pin 64 or equivalent structure, which, in the assembled state of the pivot mechanism, as shown in FIG. 3, engages in a complimentary configured slot 15 provided at the neighboring end of the column or upstanding tube 10, so that this pressure ring 60 is rigidly connected for rotation with the column or upstanding tube 10.

Having now had the benefit of the foregoing description of the inventive arrangement there will be described the operation of the pivot mechanism which is as follows:

As will be apparent from the showing of FIG. 3, the force of the spring 65 presses the pressure ring 60 against the contact or impact surface 37 of the headpiece 30 and also presses at the opposite spring end the bolt 75 against one wall of the bore 54 of the first axle body 50. Between the pressure ring 60 and the contact surface 37 there is preferably arranged a disc 59 formed of plastic having good sliding properties, for instance, "TEFLON" (polytetrafluoroethylene), whereas the disc 71, during the rotational movement in the direction of the double-headed arrow P, prevents rotation of the ring 70 relative to the ring 70', ring 70 confronting the spring 65. The spring force which is effective by means of the pressure ring 60 against the contact or impact surface 37 of the headpiece 30 is adequate for braking the housing 110 which is rotatable about the vertical lengthwise axis A in the direction of the double-headed arrow P. At the same time by means of the force of the spring 65, which is essentially supported by the pressure ring 60 at the headpiece 30, the second axle body 40 which is operatively connected with the first axle body 50 and positioned by the sliding element 45 is pressed against both inner edges or friction surfaces 35' and 35" of the bore 35. The second axle body 40 will be seen to have an outer diameter which is preferably somewhat smaller than the inner diameter of the bore 35. The forces which act from the sliding element 45 upon the axle body 40 as well as from such axle body upon the edges or friction surfaces 35', 35" of the headpiece 30 are simultaneously sufficient for braking the housing 110 which can be rocked or pivoted about the horizontal lengthwise axis A' in the direction of the double-headed arrow P' and along the line or double-headed arrow 25.

The sliding element 45 arranged in the recess 41 serves to also fix the headpiece 30 and the first axle body 50 upon the second axle body 40. The pivot mechanism or pivot arrangement 20 can be retracted with the housing 110 as a unit out of the upright tube or column 10 of the support 150, and the centering ring 80, which engages by means of its ring-shaped bead 81 in the ring-shaped groove 53 of the first axle body 50, serves as a guide or guide means. Upon insertion of the pivot mechanism 20 in the stand or upright element 150 the pins 64 engage with the appropriately configured slots 15 provided at the column 10 and serve to provide a rigid rotatable connection of the upright tube or column 10 with the pressure ring 60.

While there are shown and described present preferred embodiments of the invention, it is to be distinctly understood that the invention is not limited thereto, but may be otherwise variously embodied and practiced within the scope of the following claims.

Accordingly, What we claim is:

1. A pivot mechanism for pivotably laterally securing a housing at a stand, comprising:
   a first axle body;
   a second axle body;
   said second axle body being rotatably mounted at one end in the first axle body;
   said second axle body being capable of being operatively connected at its other end with the housing;
   a headpiece;
   means for mounting the first axle body and the second axle body in said headpiece such that the housing can be horizontally rotated about an essentially vertical lengthwise axis of the first axle body and vertically pivotable about an essentially horizontal lengthwise axis of the second axle body;
   means providing at least one friction surface for the headpiece for horizontal rotational movement of the housing about said vertical lengthwise axis;
   means providing further friction surfaces for the headpiece for vertical pivotal movement of the housing about said horizontal lengthwise axis; and
   only a single resilient element for braking said movements of the housing.

2. The pivot mechanism as defined in claim 1, wherein:
   said resilient element comprises a pressure spring.

3. The pivot mechanism as defined in claim 2, wherein:
   for braking the horizontal rotational movement of the housing said at least one friction surface defines a substantially ring-shaped friction surface formed at the headpiece;
   said stand having an upright tube;
   a pressure ring rigidly connected for rotation with said upright tube of said stand;
   said pressure ring bearing against said ring-shaped friction surface of the headipiece.

4. The pivot mechanism as defined in claim 1, wherein:
   for braking the vertical pivotal movement of the housing said further friction surfaces are operatively associated with the second axle body and cooperate with a sliding element provided at the first axle body; and
   a friction surface provided at the second axle body.

5. The pivot mechanism as defined in claim 4, wherein:
   said friction surface provided at the second axle body comprises a recess.

6. The pivot mechanism as defined in claim 4, wherein:
   said headpiece is provided with a first bore for receiving the first axle body;
   said headpiece is provided with a second bore arranged essentially transversely with respect to said first bore;
   said second bore receiving the second axle body;
   said second bore having two edges constituting said further friction surfaces;
   said second bore having a substantially groove-like recess at a side of the headpiece directed towards an underside thereof and extending essentially in radial direction.

7. The pivot mechanism as defined in claim 6, wherein:
   said second axle body is positioned in radial direction and secured against axial displacement by means of the sliding element operatively associated with the first axle body.

8. The pivot mechanism as defined in claim 1, further including:
   a stand having an upright tube provided for the housing;
   a pressure ring cooperating with the first axle body;
   said first axle body having a lower end;
   a centering ring mounted at the lower end of the first axle body;
   said pivot mechanism being centrally guided by means of the pressure ring and the centering ring in the upright tube of the stand.

9. A pivot mechanism for pivotably laterally securing a housing at a stand, comprising:
   a first body;
   a second body;
   said second body being rotatably mounted at one end in the first body;
   said second body being capable of being operatively connected at its other end with the housing;
   a headpiece;
   means for mounting the first body and the second axle body in said headpiece such that the housing can be horizontally rotated about an essentially vertical axis of the first body and vertically pivotable about an essentially horizontal axis of the second body;
   means providing at least one friction surface for the headpiece for horizontal rotational movement of the housing about said vertical lengthwise axis;
   means providing further friction surfaces for the headpiece for vertical pivotal movement of the housing about said horizontal lengthwise axis; and
   a single resilient means for braking said movements of the housing.

* * * * *